United States Patent
Miyauchi et al.

(10) Patent No.: US 12,152,274 B2
(45) Date of Patent: Nov. 26, 2024

(54) QUALITY MANAGEMENT METHOD FOR REGENERATION MEDICAL PRODUCT OR THE LIKE BY USING STANDARDIZED EXPRESSION AMOUNT

(71) Applicant: PharmaBio Corporation, Aichi (JP)

(72) Inventors: Hidemasa Miyauchi, Aichi (JP); Hitoshi Kusano, Aichi (JP)

(73) Assignee: PharmaBio Corporation, Aichi (JP)

( * ) Notice: Subject to any disclaimer, the term of this patent is extended or adjusted under 35 U.S.C. 154(b) by 0 days.

(21) Appl. No.: 16/651,927

(22) PCT Filed: Sep. 28, 2018

(86) PCT No.: PCT/JP2018/036497
§ 371 (c)(1),
(2) Date: Mar. 27, 2020

(87) PCT Pub. No.: WO2019/066044
PCT Pub. Date: Apr. 4, 2019

(65) Prior Publication Data
US 2020/0308626 A1 Oct. 1, 2020

(30) Foreign Application Priority Data
Sep. 29, 2017 (JP) .................... 2017-191049

(51) Int. Cl.
*C12Q 1/686* (2018.01)
*C12Q 1/6876* (2018.01)

(52) U.S. Cl.
CPC .......... *C12Q 1/686* (2013.01); *C12Q 1/6876* (2013.01); *C12Q 2561/113* (2013.01); *C12Q 2600/16* (2013.01)

(58) Field of Classification Search
CPC .......... C12Q 2545/101; C12Q 1/6851; C12Q 1/686; C12Q 1/6876; C12Q 2561/113; C12Q 2600/16
See application file for complete search history.

(56) References Cited

U.S. PATENT DOCUMENTS

2015/0247124 A1* 9/2015 Snoeck ................ C12N 5/0689
435/29
2017/0226479 A1* 8/2017 Badja ................... C12N 5/0696

FOREIGN PATENT DOCUMENTS

| JP | 2005-508505 A | 3/2005 |
| JP | 2014-230493 A | 12/2014 |
| WO | WO 2016/116850 A1 | 7/2016 |
| WO | WO 2016/180788 A1 | 11/2016 |

OTHER PUBLICATIONS

Whelan et al., "A method for the absolute quantification of cDNA using real-time PCR," Journal of Immunological Methods, vol. 278, pp. 261-269. (Year: 2003).*

Dhanasekaran et al., "Comparison of different standards for real-time PCR-based absolute quantification," Journal of Immunological Methods, vol. 354, pp. 34-39. (Year: 2010).*
Fraga et al., "Real-Time PCR," Current Protocols Essential Laboratory Techniques, Unit 10.3, pp. 10.3.1-10.3.34. (Year: 2008).*
Haddad-Mashadrizeh et al., "Evidence for crossing the blood barrier of adult rat brain by human adipose-derived mesenchymal stromal cells during a 6-month period of post-transplantation", Cytotherapy, vol. 15, No. 8, pp. 951-960 (2013).
Jung et al., "Ablation of tumor-derived stem cells transplanted to the central nervous system by genetic modification of embryonic stem cells with a suicide gene" Human Gene Therapy, vol. 18, No. 12, pp. 1182-1192 (2007).
K Kruczek, "Differentiation and transplantation of mouse embryonic stem cell-derived cone photoreceptor precursors" Feb. 28, 2017, Retrieved from the Internet: URL:https://discovery.ucl.ac.uk/id/eprint/1542163/1/Thesis%20fill%20v2%20-%20Final.pdf [retrieved on Apr. 30, 2021].
Kuai et al., "Transplantation of mouse embryonic stem cell-derived oligodendrocytes in the murine model of globoid cell leukodystrophy" Stem Cell Research & Therapy, Biomed. Central Ltd., vol. 6, No. 1, p. 30 (2015).
Ragina et al., "Downregulation of H19 Improves the Differentiation Potential of Mouse Parthenogenetic Embryonic Stem Cells" Stem Cells and Development, vol. 21, No. 7, pp. 1134-1144 (2012).
Schrobback et al., "Effects of oxygen and culture system on in vitro propagation and redifferentiation of osteoarthritic human articular chondrocytes" Cell and Tissue Research, vol. 347, No. 3, pp. 649-663 (2011).
Supplementary European Search Report issued in Application No. EP 18863066, dated May 11, 2021.
Leong, D. T. et al., "Absolute quantification of gene expression in biomaterials research using real-time PCR", Biomaterials, 2007, vol. 28, pp. 203-210, p. 205, left column, "2. 5. Primer design and standards preparation", fig. 2 (e).
ThermoFisher Scientific, [retrieved on Dec. 11, 2018], Internet <URL:https://www.learningatthebench.com/qpcrbasic5.html>, entire text, non-official translation ("Principle of real-time PCR, Now is the time for understanding in earnest and thoroughly!, The 5th Real-time PCR course"), published on Sep. 16, 2015.

* cited by examiner

*Primary Examiner* — Young J Kim
(74) *Attorney, Agent, or Firm* — KNOBBE, MARTENS, OLSON & BEAR LLP

(57) ABSTRACT

In order to perform relative quantification of gene expression in a cell/tissue repeatedly, it is required to supply a large number of standards. By employing an absolutely quantified standard including a synthetic DNA plasmid or the like, the present invention stably provides uniform standards for the repeated gene expression analysis over a long period of time. Further, the present invention enables stable execution of repeated gene expression analysis with high reproducibility by using such a standard. In addition, the present invention provides a method for stably controlling the quality of a cell or tissue over a long period of time by using the method, and also provides a standard used for the method.

7 Claims, 2 Drawing Sheets

QUALITY MANAGEMENT METHOD FOR REGENERATION MEDICAL PRODUCT OR THE LIKE BY USING STANDARDIZED EXPRESSION AMOUNT

TECHNICAL FIELD

The present invention provides a method for stably performing gene expression analysis in gene expression analysis of a cell or a tissue, by using an absolutely quantified standard, for example, a standard including an absolutely quantified DNA plasmid, a method for stably controlling the quality of a cell or a tissue over a long period of time by using the method, and a standard for use in the method.

BACKGROUND ART

Cultured cells of a mammal or the like are widely used in the fields of medicine, research, and the like, and cells may deteriorate during the culture and storage. In order to confirm that cells are not deteriorated during the culture and storage, it is widely performed to control and ensure the quality of cells by gene expression analysis using real-time PCR (Patent Literature 1).

In a real-time PCR assay for use in such a gene expression analysis, relative quantification using a calibration curve method or a comparative Ct method has been widely used. In a calibration curve method, serially diluted RNA extracted from a sample (cell) that highly expresses both of internal standard genes and target genes, or serially diluted cDNA synthesized from the RNA, is used as a standard. In a case of relative quantification, it is required to compare a reference calibrator sample with a target sample for each gene.

In performing research on a specific cell over a long period of time, in order to repeatedly perform relative quantification of gene expression as accurately as possible throughout the entire period of time, it is desirable to prepare a large amount of standards or calibrator samples in the initial stage of the research, and to use stored aliquots from the same cDNA/RNA pool in each gene expression analysis. However, it is difficult to obtain a sufficient amount of standards or calibrators to be required throughout the life cycle over a long period from development to market launch, and to stably store and maintain the obtained standards or calibrator samples. This is thus not realistic.

Further, in the regenerative medicine area and the like, the need for supplying a large amount of cells having a specific property over a long period of time has been increased, and gene expression analysis is used to control the quality of cells (Patent Literature 2). It is difficult to supply a large amount of standards or calibrators to be required for the gene expression analysis for use in quality control of these cells, and a better method has been demanded.

In addition, in a case where cells/tissues of which the quality should be ensured are maintained in a large amount, it is assumed that these cells/tissues are required to be controlled in physically separated facilities, and when the quality control of cells is performed individually in these remote facilities, stable transfer of standards or calibrators may also become a problem.

CITATION LIST

Patent Literature

Patent Literature 1: JP 2005-508505 A
Patent Literature 2: JP 2014-230493 A

SUMMARY OF INVENTION

Technical Problem

As for a cell/tissue to be used in research over a long period of time, in order to repeatedly perform relative quantification of gene expression of the cell/tissue as accurately as possible throughout the entire period of research, a large amount of standard or calibrator samples are required, and it is difficult to supply such a large amount of standards.

In particular, in the regenerative medicine area, the quality control to maintain constantly the property of a large amount of cells/tissues to be used over a long period of time is important, and in order to check that there is no change in the gene expression pattern of a cell, it is required to perform the gene expression analysis at fixed time intervals over a long period of time. A technique that enables the repeated gene expression analysis to be more stably performed over such a long period of time has been required.

Solution to Problem

The present invention stably provides uniform standards for the repeated gene expression analysis over a long period of time by employing an absolutely quantified standard including a synthetic DNA plasmid or the like. Further, the present invention enables the repeated gene expression analysis to be stably performed with high reproducibility by using such a standard.

Advantageous Effects of Invention

By using the method according to the present invention, the quality of a cell having a specific property can be ensured over a long period of time, and thus the method is extremely useful in the field where cells having a specific property are required to be supplied in a large amount over a long period of time, for example, in the regenerative medicine area.

In addition, the method according to the present invention enables the efficacy or safety of a regenerative medicine product to be evaluated with high accuracy. Further, by using a synthetic DNA plasmid as the absolutely quantified standard, the repeated gene expression analysis over a long period of time can be performed stably while the standard can be prepared in each facility when performing the quality control of cells individually in a remote facility.

In addition, by employing an absolutely quantified standard, a sample for comparison is not necessarily required, and thus the evaluation can be performed with a standardized expression level obtained by dividing the copy number of a target gene in a target sample by the copy number of an internal standard gene, each of which has been obtained using a calibration curve.

DETAILED DESCRIPTION OF THE PREFERRED EMBODIMENTS

Figure 1:
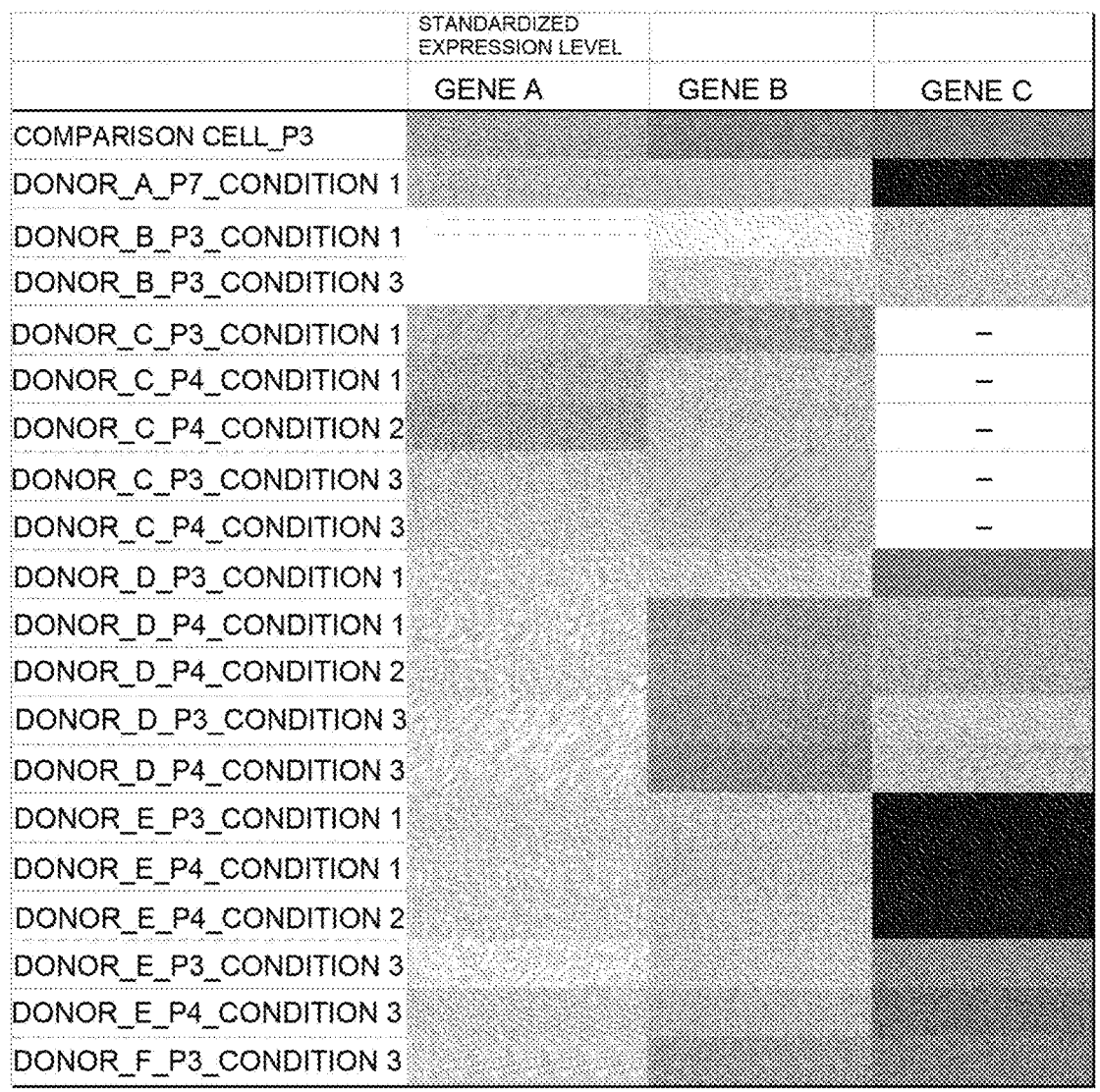
FIG. 1 shows results of gene expression analysis of genes A to C in somatic stem cells isolated and cultured from tissues collected from donors A to F, and in a commercially available fibroblast derived from the same tissue. The standardized expression levels standardized by dividing the expression levels of respective target genes by the expression levels of the internal standard genes are shown by a heat map (the lower expression level is shown in darker and the higher expression level is shown in brighter).

In one aspect, the present invention is a method for analyzing gene expression in a cell or a tissue containing a cell, including using an absolutely quantified standard.

Further, in another aspect, the present invention is the method for analyzing gene expression described above, in which the method uses real-time PCR.

In addition, in another aspect, the present invention is the method for analyzing gene expression described above, in which the absolutely quantified standard being a synthetic DNA is used.

Further, in another aspect, the present invention is the method for analyzing gene expression described above, in which the absolutely quantified standard being a DNA plasmid is used.

In addition, in another aspect, the present invention is a method for controlling quality of a cell or a tissue containing a cell, by using the method for analyzing gene expression described above.

Further, in another aspect, the present invention is a method for controlling quality of a cell or a tissue containing a cell, in which the cell is a mammal cell.

In addition, in another aspect, the present invention is a method for controlling quality of a cell or a tissue containing a cell, in which the cell is a somatic stem cell.

Further, in another aspect, the present invention is a method for controlling quality of a cell or a tissue containing a cell, in which the cell or the tissue is used in the regenerative medicine area.

In addition, in another aspect, the present invention is a method for evaluating efficacy or safety of a regenerative medicine product containing a cell, by using the method for analyzing gene expression described above.

Further, in another aspect, the present invention is one or multiple absolutely quantified standards used in the above method for analyzing gene expression, the above method for controlling quality of a cell or a tissue containing a cell, or the above method for evaluating efficacy or safety of a regenerative medicine product.

Definition

In the present invention, the expression "gene expression analysis" includes creating a population of what are derived from a cell or tissue sample and analyzing the population to determine which gene is expressed in the sample. Typically, by examining the presence of mRNA derived from each gene in the sample, the expression of the gene is evaluated.

The expression "quantitative gene expression analysis" means analysis to determine the relative or absolute value of the expression level of a gene. For example, the "quantitative gene expression analysis" includes analysis to determine the expression level of a gene based on the mRNA level in a sample.

The expression "PCR" or "polymerase chain reaction" means a technique for replicating a selected specific small fragment of DNA in vitro, even in the presence of excessive non-specific DNA. When primers are added to the selected DNA, the primers initiate duplication of the selected DNA by using nucleotides, a polymerase, and the like. By cycling the temperature, the selected DNA repeats denaturation and duplication. In some cases, a linear amplification method may be used as a substitute for PCR.

The expression "real-time PCR" means various PCR applications in which amplification in PCR is measured during the reaction rather than after completion of the reaction. In gene expression analysis using real-time PCR, the abundance of mRNA in a sample is calculated, and the gene expression level is determined. At this time, RNA itself may be used as a template for PCR, or a cDNA that has reverse transcribed from RNA may be used as a template for PCR. In a case where RNA is used as the template, a RT-PCR reaction solution in which a reverse transcriptase is added to a PCR reaction solution is prepared, and a cDNA is synthesized with the use of the RNA as the template by a reverse transcription reaction before being applied to temperature cycling of PCR reaction, and then a target sequence can be amplified with the use of the cDNA as the template by the subsequent PCR reaction (1-step RT-PCR). Further, the reverse transcription reaction and the PCR reaction can be separately performed (2-step RT-PCR). As the real-time PCR method, it is not particularly limited, and for example, a method of using a template-dependent nucleic acid polymerase probe, for example, a probe such as a hydrolysis probe using 5'-exonuclease activity of Taq DNA polymerase, a method of using an intercalator such as SYBR Green, or the like can be used.

The expression "target gene" means a gene to be subjected to measurement of the abundance of the corresponding mRNA in real-time PCR.

The expression "internal standard gene" means a gene of which the expression level is measured to correct the expression level between experiments in real-time PCR. Typically, as the internal standard gene, a gene that is expressed in a certain amount in common in many tissues and cells, constantly expressed at all times, and essential for the maintenance and growth of cells (housekeeping gene), is used.

The expression "standard" means a sample used for obtaining a calibration curve showing the relationship between the Ct value (the number of cycles when the amplification curve reaches a constant signal intensity) and the copy number in the gene sample in real-time PCR, and is constituted of a dilution series. Typically, the standard contains RNA extracted from a sample (cell) that highly expresses both of an internal standard gene and a target gene, or a cDNA synthesized from the RNA by reverse transcription, and also contains newly synthesized RNA or DNA.

The expression "calibration sample" means a sample arbitrarily selected as a reference when the relative abundance of a target gene in multiple samples is measured.

The expression "expression profile" means a measurement result of the abundance ratio of multiple cell components. For example, the expression profile means the abundance of multiple RNAs or proteins, or of a combination of multiple RNAs and proteins. The expression profile may be a measurement result of, for example, the transcription state or the translation state.

The expression "quality control" includes maintaining a cell and a tissue having constant properties by confirming that the cell and tissue maintain the constant properties, by removing the cells and tissues that have lost the properties, and the like. Whether or not the constant properties are maintained is typically determined based on the uniformity of the expression profiles of genes of the cell and tissue.

The expression "cell" means a smallest structural unit of an organism that is constituted of one or more nuclei, cytoplasm, and various organelles, and the whole parts are surrounded by a semipermeable cell membrane or a cell wall, and can independently function, or means a unicellular organism. The cell may be a prokaryote, a eukaryote, or an archaeon. As the cell, a mammalian cell, in particular, a human cell is preferred. The cell may be a natural cell, or may be a cell modified to achieve the desired property, for example, by genetic manipulation or by successive cultivation.

Absolutely Quantified Standard

The absolutely quantified standard of the present invention means a standard in which the content (the number of molecules) of RNA or DNA or an analog thereof, serving as a template for PCR reaction and being contained in each sample of a dilution series of a standard to be used in real-time PCR, has been determined in advance.

As the RNA or DNA or an analog thereof, ones in various forms such as single-stranded form, double-stranded form, straight chain form, and circular form can be used, and preferably, a circular plasmid DNA can be used. Further, the RNA or DNA or an analog thereof may contain a non-natural base pair.

The RNA or DNA to be used for the standard can have a sequence of a target gene and/or a sequence of an internal standard gene. A person skilled in the art can appropriately select such a sequence based on a known method. For example, a person skilled in the art can synthesize RNA or DNA by experiment, or by using a primer and the like determined with the use of sequence data and the like of a publicly available nucleotide sequence database (NCBI, GenBank, and the like), and amplify the RNA or DNA having a desired sequence by PCR, or can newly synthesize RNA or DNA.

In addition, as the method for determining the content of RNA or DNA, it is not particularly limited, and a known method can be used, for example, a method for measuring the absorbance of a specific absorption wavelength of a nucleic acid by using a spectrophotometer, a method for measuring the fluorescence emitted when bound to a specific target molecule (for example, Qubit fluorometer (Invitrogen)), a method in which nucleic acid subjected to agarose gel electrophoresis is stained, and the concentration of the stained nucleic acid is measured, a method of microchip-type electrophoresis (for example, Experion DNA analysis kit manufactured by Bio-Rad Laboratories, Inc.), or the like can be used. In particular, microchip-type electrophoresis is preferably used.

The quantification of the standard by such a known method can be performed repeatedly with high accuracy, and for example, even in a case where a newly absolutely quantified standard is synthesized and used, comparison with the result of the analysis performed by using a standard that has been previously used can be performed.

Calculation of Expression Level of Target Gene

When the expression level of a target gene is calculated by using the absolutely quantified standard of the present invention, the expression level (copy number) of target gene in the sample can be calculated by applying the Ct value obtained from a sample of which the content is unknown, to a calibration curve created by using the standard.

Any known method can be used to create a calibration curve and for example, a calibration curve can be created by using an amplification curve, where the amplification curve showing the relationship between the number of cycles and the amount of amplified DNA is obtained from the result of real-time PCR of a dilution series of a standard.

Further, by obtaining the expression level of an internal standard gene of each sample of which the expression level of a target gene has been obtained in the similar way, thereby standardizing the expression level of the target gene in each sample with the expression level of the standard gene, it is possible to obtain the standardized expression level of the target gene in which the variation between the respective samples has been corrected.

In addition, in order to examine the difference in the expression level of each target gene between various cells, it is possible to calculate the relative expression level to the comparison cell by dividing the standardized expression level of the cell to be analyzed by the value of a comparison cell.

Application to Quality Control of Cell and Tissue

When a cell or a tissue is cultured and stored over a long period of time, the expression levels of multiple genes constituting a gene expression profile that characterizes each cell or tissue are obtained at fixed time intervals by the above method, and by confirming that there is no or slight change over time, it can be confirmed and ensured that the cell or tissue has not been deteriorated.

Here, the type of and the number of multiple genes constituting a gene expression profile that characterizes each cell or tissue can be arbitrarily selected by a person skilled in the art based on known information.

As such a cell, any cell can be selected. Preferably, the cell is a mammal cell, in particular, a human cell. Further, the cell is preferably a somatic stem cell, or is in addition, preferably a cell that is used in the regenerative medicine area.

In such a quality control, by using a synthetic DNA as the absolutely quantified standard, the quality of the cell can be controlled by a unified reference even when the cell or tissue is controlled in a different facility.

Application to Evaluation of Efficacy or Safety of Regenerative Medicine Product In a regenerative medicine product containing a cell, in order to exert a desired therapeutic effect, a cell is necessary to maintain a constant property. By using a method for analyzing gene expression with the use of the absolutely quantified standard of the present invention, by confirming that there is no or slight change over time of an expression profile of the cell contained in a regenerative medicine product, evaluation for determining whether or not the cell maintains a constant property is performed, that is, the efficacy of a regenerative medicine product containing the cell can be evaluated. In such cases, for example, in a case where evaluation is performed on the basis of the amount of change in the relative or absolute expression level of a specific gene (group), the standard of the amount change can be set to, but not limited to, 200%, 100%, 90%, 80%, 70%, 60%, 50%, 40%, 30%, 20%, 10%, 5%, 3%, 2%, 1%, 0.5%, 0.1%, or the like.

In addition, the application of a deteriorated cell causes a high risk of losing the safety of a regenerative medicine product. By using a method for analyzing gene expression with the use of the absolutely quantified standard of the present invention, the deteriorated cell is detected, and the safety of a regenerative medicine product can be evaluated.

Absolutely Quantified Standard and Kit Containing the Same

A set of absolutely quantified standards selected for quality control of a specific cell or tissue is provided as a set of standards or as a single standard, for use in quality control of the cell or tissue.

When the set of absolutely quantified standards is provided as a set of standards or as a single standard, an additive agent that is usually used, such as a preservative can be used in combination, and the set can be provided in any form of a liquid, a dry powder, or the like.

The present invention will be described in more detail in the following Examples.

EXAMPLES

Preparation of Somatic Stem Cell

For each somatic stem cell isolated from a tissue that had been collected from each of donors A to F, a sample was prepared from each of the cells having different culture conditions (conditions 1 to 3) and different passage numbers (P3, P4, and P7).

For the prepared DNA samples, the expressions of genes A to C were analyzed by real-time PCR according to the following procedures. Further, a commercially available fibroblast (comparison cell P3) derived from the same tissue was cultured, and similarly analyzed as the comparison cell.

RNA Extraction:

RNA was extracted from a cell culture flask of 80% confluent by the following procedures. A medium in the flask was removed, and the flask was washed with DPBS(−) twice, and then 900 μL of Buffer RLT (QIAGEN) was added to the washed flask, cells were peeled off by using a cell scraper, and a cell lysate was recovered in a 1.5-mL tube. From this cell lysate, RNA was extracted by using RNeasy Mini Kit (QIAGEN) (genomic DNA was removed by using RNase-Free DNase Set (QIAGEN)), and finally the RNA was eluted with 30 μL of RNase free water.

Reverse Transcription Reaction:

By using an RNA solution, reverse transcription was performed with the use of QuantiTect Reverse Transcriptase kit (QIAGEN) to prepare a cDNA. In the reverse transcription reaction, a reaction volume of 40 μL and 2 μg of total RNA were used.

Preparation of Absolutely Quantified DNA Standard:

A plasmid in which a target sequence of each of genes containing an internal standard gene had been cloned was linearized and purified, and quantified by using a microchip-type electrophoresis device (Experion DNA analysis kit, Bio-Rad), and the concentration (ng/μL) obtained based on the molecular weight was converted to the copy number.

Gene Expression Analysis by Calibration Curve Method:

A primer-probe mix (in-house design) of the cryopreserved TaqMan Gene Expression Assay (target genes A to C) and the internal standard gene were thawed on ice, and a PCR reaction master mix was prepared for each gene on ice by using TaqMan Fast Advanced Master Mix (Thermo Fisher Scientific). The master mix was aliquoted into respective wells of PCR tubes by 15 μL each, and the reverse transcription reaction solution prepared and diluted in advance (Nkx2.5: undiluted solution of reverse transcription reaction solution, GATA4, Tbx5, Mef2C: 20-fold dilution, ACTB: 100-fold dilution; n=2 each), or a standard solution ($10^1$ to $10^5$ copies/μL; n=1 each) was added into the respective wells by 5 μL each. The prepared PCR tubes were set in ABI7500 (Thermo Fisher Scientific), and were subjected to real-time PCR analysis.

In accordance with a conventional method, the copy numbers of each target gene and the internal standard gene in the reaction solution were calculated based on the calibration curve created for each gene. The standardized expression level of each target gene was calculated through the standardization where the obtained copy number of each target gene was divided by the copy number of the internal standard gene.

Evaluation of Gene Expression Profile:

For the somatic stem cell sample derived from each donor, gene expression analysis was performed for each target gene by a calibration curve method, and the standardized expression level of each target gene was calculated.

In a similar manner, as a comparison, also for a fibroblast (comparison cell P3) derived from the same tissue as that of the above-described somatic stem cell, gene expression analysis was performed for each target gene by a calibration curve method and the standardized expression level of each target gene was calculated.

For each target gene, the relative expression level to the comparison cell was calculated by standardization where the standardized expression level in the somatic stem cell sample was divided by the standardized expression level in the comparison cell.

Results:

The test was considered valid when the coefficient of determination R2 of each calibration curve is 0.98 or more.

The standardized expression levels are shown in FIG. 1 by a heat map (the lower expression level is shown in darker and the higher expression level is shown in brighter). Gene expression profiles that are different from each other depending on each donor and the sample preparation condition were obtained.

Figure 2:
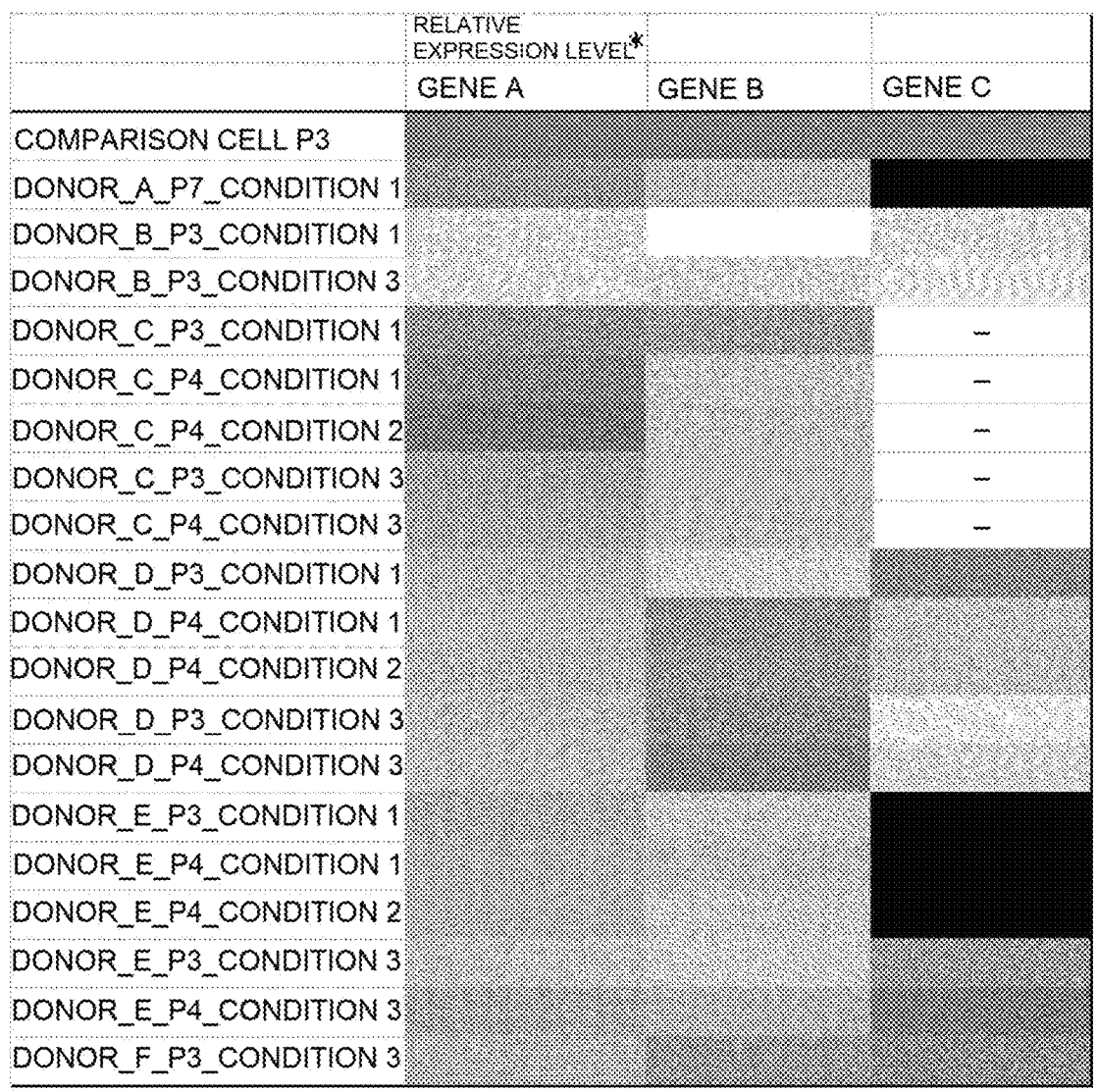
FIG. 2 shows relative expression levels of the target genes in respective samples to a comparison cell by a heat map. By dividing the standardized expression level of the target gene in each sample by the standardized expression level of the target gene in a comparison cell, the relative expression level to the comparison cell was calculated.

The relative expression levels to a target gene in a comparison cell are shown in FIG. 2 by a heat map. With respect to each target gene, the difference in the expression profile depending on each donor and the sample preparation condition is clearly shown.

In the method for analyzing gene expression with the use of the absolutely quantified standard of the present invention, the state of each sample cell can be evaluated with the standardized expression level not necessarily with obtaining the relative expression level with the comparison cell.

The description of the present invention and the description of Examples in the present specification are for the purpose of detailed description of various exemplary embodiments of the present invention, and a person skilled in the art can make various improvements and modifications in the embodiments disclosed in the present specification without departing from the scope of the present invention. Therefore, the description of the present specification does not limit the scope of the present invention in any way, and the scope of the present invention is determined only by the scope of claims.

What is claimed is:

1. A method for analyzing an expression of a target gene in a cell or a tissue containing a cell, comprising:
   preparing a sample including mRNA expressed from the target gene isolated from the cell;
   preparing a dilution series of an absolutely quantified standard having a sequence of the target gene;
   preparing a sample including mRNA expressed from a sequence of internal standard gene other than the target gene;
   preparing a dilution series of an absolutely quantified standard having the sequence of an internal standard gene;
   for each of the dilution series of an absolutely quantified standard having a sequence of the target gene and the dilution series of an absolutely quantified standard having the sequence of an internal standard gene, obtaining an amplification curve showing a relationship between the number of cycles when the amplification curve reaches a constant rate of increase of signal intensity (Ct value) and an amount of amplified DNA from a result of real-time PCR of the dilution series of the absolutely quantified standard, and creating a calibration curve based on the amplification curve;

amplifying the mRNA expressed from the target gene in the sample to determine a Ct value of the mRNA in the sample;

calculating an expression level of the target gene based on the Ct value of the mRNA in the sample and the calibration curve; and obtaining the expression level of the internal standard gene of each sample of which the expression level of the target gene has been obtained based on the Ct value of the mRNA of the internal standard gene in the sample and the calibration curve, thereby standardizing the expression level of the target gene in each sample with the expression level of the standard gene, to obtain the standardized expression level of the target gene in which a variation between the respective samples has been corrected.

2. The method for analyzing gene expression according to claim 1, wherein amplifying the mRNA expressed from the target gene in the sample is carried out in real-time RT-PCR analysis.

3. The method for analyzing gene expression according to claim 1, wherein the absolutely quantified standard having the sequence of the target gene and the absolutely quantified standard having the sequence of the internal standard gene are respectively a synthetic DNA.

4. The method for analyzing gene expression according to claim 3, wherein the synthetic DNA is a DNA plasmid.

5. The method according to claim 1, wherein the cell is a mammal cell.

6. The method according to claim 5, wherein the cell is a somatic stem cell.

7. A method for evaluating efficacy or safety of a regenerative medicine product containing a cell, comprising:

analyzing gene expression according to claim 1; and evaluating efficacy or safety of the regenerative medicine product containing the cell by determining whether or not the cell maintains a constant property.

* * * * *